US009028476B2

(12) United States Patent  (10) Patent No.: US 9,028,476 B2
Bonn  (45) Date of Patent: May 12, 2015

(54) DUAL ANTENNA MICROWAVE RESECTION AND ABLATION DEVICE, SYSTEM AND METHOD OF USE

(75) Inventor: Kenlyn S. Bonn, Arvada, CO (US)

(73) Assignee: Covidien LP, Mansfield, MA (US)

( * ) Notice: Subject to any disclaimer, the term of this patent is extended or adjusted under 35 U.S.C. 154(b) by 1078 days.

(21) Appl. No.: 13/020,664

(22) Filed: Feb. 3, 2011

(65) Prior Publication Data

US 2012/0203218 A1    Aug. 9, 2012

(51) Int. Cl.
    A61B 18/18    (2006.01)
    H01Q 1/52     (2006.01)
    H01Q 9/16     (2006.01)
    H01Q 21/30    (2006.01)
    A61B 18/00    (2006.01)

(52) U.S. Cl.
    CPC ............ *H01Q 1/521* (2013.01); *A61B 18/1815* (2013.01); *A61B 2018/00577* (2013.01); *A61B 2018/1838* (2013.01); *A61B 2018/1869* (2013.01); *H01Q 9/16* (2013.01); *H01Q 21/30* (2013.01); *H01Q 5/48* (2015.01)

(58) Field of Classification Search
    CPC .... A61B 18/14; A61B 18/1492; A61B 18/18; A61B 18/1815; A61B 18/183; A61B 18/1838; A61B 18/1876
    USPC ................................ 606/33–50; 607/154, 156
    See application file for complete search history.

(56) References Cited

U.S. PATENT DOCUMENTS

| 3,978,393 | A | 8/1976 | Wisner et al. |
| D263,020 | S | 2/1982 | Rau, III |
| 4,534,347 | A | 8/1985 | Taylor |
| D295,893 | S | 5/1988 | Sharkany et al. |
| D295,894 | S | 5/1988 | Sharkany et al. |

(Continued)

FOREIGN PATENT DOCUMENTS

| CN | 1103807 A | 6/1995 |
| DE | 390937 C | 3/1924 |

(Continued)

OTHER PUBLICATIONS

European Search Report for European Application No. 12000335.5 dated Apr. 27, 2012.

(Continued)

*Primary Examiner* — Ronald Hupczey
*Assistant Examiner* — Khadijeh Vahdat

(57) ABSTRACT

A system for generating microwave energy includes a microwave generator that generates first and second microwave signals, a transmission line and a dual antenna microwave device. The transmission line transmits the first and second microwave signals to the microwave device. The microwave device includes a first antenna proximal a second antenna and a dual-sided choke positioned therebetween. The first antenna receives the first microwave signal from the transmission line between a first conductor and a second conductor and the second antenna receives the second microwave signal between the second conductor and a third conductor. The dual-sided choke includes a first and a second antenna choke circuit. The first antenna choke circuit limits the propagation of electromagnetic fields generated by the first antenna toward the second antenna and the second antenna choke circuit limits the propagation of electromagnetic fields generated by the second antenna toward the first antenna.

30 Claims, 10 Drawing Sheets

(56) References Cited

U.S. PATENT DOCUMENTS

| | | |
|---|---|---|
| 5,301,687 A | 4/1994 | Wong et al. |
| 5,902,251 A | 5/1999 | vanHooydonk |
| 5,938,692 A | 8/1999 | Rudie |
| 5,974,343 A | 10/1999 | Brevard et al. |
| D424,694 S | 5/2000 | Tetzlaff et al. |
| D425,201 S | 5/2000 | Tetzlaff et al. |
| 6,208,903 B1 | 3/2001 | Richards et al. |
| 6,222,356 B1 | 4/2001 | Taghizadeh-Kaschani |
| 6,226,553 B1 | 5/2001 | Carl et al. |
| D449,886 S | 10/2001 | Tetzlaff et al. |
| D457,958 S | 5/2002 | Dycus et al. |
| D457,959 S | 5/2002 | Tetzlaff et al. |
| 6,582,427 B1 | 6/2003 | Goble et al. |
| D496,997 S | 10/2004 | Dycus et al. |
| D499,181 S | 11/2004 | Dycus et al. |
| D525,361 S | 7/2006 | Hushka |
| D531,311 S | 10/2006 | Guerra et al. |
| D533,942 S | 12/2006 | Kerr et al. |
| D535,027 S | 1/2007 | James et al. |
| D541,418 S | 4/2007 | Schechter et al. |
| D541,938 S | 5/2007 | Kerr et al |
| D564,662 S | 3/2008 | Moses et al. |
| D606,203 S | 12/2009 | Husheer et al. |
| D613,412 S | 4/2010 | DeCarlo |
| 7,863,984 B1 | 1/2011 | Behnke |
| 8,012,148 B2 | 9/2011 | Turovskiy et al. |
| 8,034,052 B2 | 10/2011 | Podhajsky |
| 8,038,693 B2 | 10/2011 | Allen |
| 8,069,553 B2 | 12/2011 | Bonn |
| 8,188,435 B2 | 5/2012 | Podhajsky et al. |
| 8,216,227 B2 | 7/2012 | Podhajsky |
| 8,235,981 B2 | 8/2012 | Prakash et al. |
| 8,282,632 B2 | 10/2012 | Rossetto |
| 8,292,881 B2 | 10/2012 | Brannan et al. |
| 8,313,486 B2 | 11/2012 | Kim et al. |
| 8,328,799 B2 | 12/2012 | Brannan |
| 8,328,800 B2 | 12/2012 | Brannan |
| 8,328,801 B2 | 12/2012 | Brannan |
| 8,334,812 B2 | 12/2012 | Brannan |
| 8,355,803 B2 | 1/2013 | Bonn et al. |
| 8,382,750 B2 | 2/2013 | Brannan |
| 8,394,087 B2 | 3/2013 | Willyard et al. |
| 8,394,092 B2 | 3/2013 | Brannan |
| 8,409,187 B2 | 4/2013 | Bonn |
| 8,409,188 B2 | 4/2013 | Kim et al. |
| 8,430,871 B2 | 4/2013 | Brannan |
| 8,463,396 B2 | 6/2013 | Podhajsky |
| 8,469,953 B2 | 6/2013 | DeCarlo |
| 8,491,579 B2 | 7/2013 | Rossetto |
| 8,545,493 B2 | 10/2013 | Brannan et al. |
| 8,552,915 B2 | 10/2013 | Brannan |
| 8,556,889 B2 | 10/2013 | Brannan |
| 8,568,398 B2 | 10/2013 | Brannan |
| 8,568,401 B2 | 10/2013 | Brannan |
| 8,568,404 B2 | 10/2013 | Brannan |
| 8,617,153 B2 | 12/2013 | Lee et al. |
| 8,652,127 B2 | 2/2014 | Prakash et al. |
| 8,672,923 B2 | 3/2014 | Ladtkow et al. |
| 8,672,933 B2 | 3/2014 | Shiu et al. |
| 8,673,364 B2 | 3/2014 | Jalota et al. |
| 8,690,866 B2 | 4/2014 | Brannan |
| 8,728,067 B2 | 5/2014 | Prakash et al. |
| 8,740,893 B2 | 6/2014 | Shiu et al. |
| 8,764,744 B2 | 7/2014 | Brannan |
| 8,777,939 B2 | 7/2014 | Lee et al. |
| 8,834,460 B2 | 9/2014 | Peterson |
| 2002/0022836 A1 | 2/2002 | Goble et al. |
| 2003/0080916 A1 | 5/2003 | Zeilinger |
| 2003/0153908 A1 | 8/2003 | Goble et al. |
| 2005/0015081 A1* | 1/2005 | Turovskiy et al. ............. 606/33 |
| 2005/0149010 A1 | 7/2005 | Turovskiy et al. |
| 2005/0203388 A1 | 9/2005 | Carr |
| 2008/0266203 A1 | 10/2008 | Rossetto et al. |
| 2009/0076492 A1 | 3/2009 | Behnke |
| 2009/0326620 A1 | 12/2009 | Rossetto et al. |
| 2010/0023000 A1* | 1/2010 | Stevenson et al. .............. 606/33 |
| 2010/0053015 A1 | 3/2010 | Willyard |
| 2010/0217251 A1 | 8/2010 | Rossetto et al. |
| 2010/0217252 A1 | 8/2010 | Rossetto et al. |
| 2010/0331834 A1 | 12/2010 | Peterson et al. |
| 2011/0034919 A1 | 2/2011 | DeCarlo |
| 2011/0054458 A1 | 3/2011 | Behnke |
| 2011/0054459 A1 | 3/2011 | Peterson |
| 2011/0060326 A1 | 3/2011 | Smith et al. |
| 2011/0071511 A1 | 3/2011 | Brannan et al. |
| 2011/0071512 A1 | 3/2011 | Behnke, II et al. |
| 2011/0073594 A1 | 3/2011 | Bonn |
| 2011/0077633 A1 | 3/2011 | Bonn et al. |
| 2011/0077635 A1 | 3/2011 | Bonn |
| 2011/0077636 A1 | 3/2011 | Brannan et al. |
| 2011/0118731 A1 | 5/2011 | Ladtkow |
| 2011/0152853 A1 | 6/2011 | Manley et al. |
| 2011/0172659 A1 | 7/2011 | Brannan |
| 2011/0190754 A1 | 8/2011 | Kim et al. |
| 2011/0208177 A1 | 8/2011 | Brannan |
| 2011/0208180 A1 | 8/2011 | Brannan |
| 2011/0213353 A1 | 9/2011 | Lee et al. |
| 2011/0238053 A1 | 9/2011 | Brannan et al. |
| 2011/0238055 A1 | 9/2011 | Kim et al. |
| 2011/0270240 A1 | 11/2011 | Shiu et al. |
| 2011/0282336 A1 | 11/2011 | Brannan et al. |
| 2011/0295245 A1 | 12/2011 | Willyard et al. |
| 2011/0299719 A1 | 12/2011 | Podhajsky et al. |
| 2011/0301589 A1 | 12/2011 | Podhajsky et al. |
| 2011/0301590 A1 | 12/2011 | Podhajsky et al. |
| 2011/0301591 A1 | 12/2011 | Podhajsky et al. |
| 2011/0319880 A1 | 12/2011 | Prakash et al. |
| 2012/0016359 A1 | 1/2012 | Podhajsky |
| 2012/0016360 A1 | 1/2012 | Brannan |
| 2012/0059365 A1 | 3/2012 | Cunningham |
| 2012/0101487 A1 | 4/2012 | Cunningham et al. |

FOREIGN PATENT DOCUMENTS

| | | |
|---|---|---|
| DE | 1099658 B | 2/1961 |
| DE | 1139927 B | 11/1962 |
| DE | 1149832 B | 6/1963 |
| DE | 1439302 A1 | 1/1969 |
| DE | 2439587 | 2/1975 |
| DE | 2455174 | 5/1975 |
| DE | 2407559 A1 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10310765 | 9/2004 |
| DE | 10328514 | 3/2005 |

(56) References Cited

FOREIGN PATENT DOCUMENTS

| | | |
|---|---|---|
| DE | 102004022206 | 12/2005 |
| DE | 202005015147 | 3/2006 |
| DE | 102009015699 | 5/2010 |
| EP | 0 246 350 | 11/1987 |
| EP | 0 521 264 | 1/1993 |
| EP | 0 556 705 | 8/1993 |
| EP | 0 558 429 | 9/1993 |
| EP | 0 836 868 | 4/1998 |
| EP | 0 882 955 | 12/1998 |
| EP | 1 159 926 | 5/2001 |
| EP | 2158868 | 3/2010 |
| FR | 179 607 | 11/1906 |
| FR | 1 275 415 | 10/1961 |
| FR | 1 347 865 | 11/1963 |
| FR | 2 235 669 | 1/1975 |
| FR | 2 276 027 | 1/1976 |
| FR | 2 313 708 | 12/1976 |
| FR | 2 502 935 | 10/1982 |
| FR | 2 517 953 | 6/1983 |
| FR | 2 573 301 | 5/1986 |
| FR | 2 862 813 | 5/2005 |
| FR | 2 864 439 | 7/2005 |
| JP | 5-5106 | 1/1993 |
| JP | 05-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09000492 | 1/1997 |
| JP | 09010223 | 1/1997 |
| JP | 11244298 | 9/1999 |
| JP | 2000342599 | 12/2000 |
| JP | 2000350732 | 12/2000 |
| JP | 2001008944 | 1/2001 |
| JP | 2001029356 | 2/2001 |
| JP | 2001128990 | 5/2001 |
| JP | 2001231870 | 8/2001 |
| JP | 2008142467 | 6/2008 |
| SU | 166452 | 11/1964 |
| SU | 401367 | 11/1974 |
| SU | 727201 | 4/1980 |
| WO | WO97/41924 | 11/1997 |
| WO | WO00/53112 | 9/2000 |
| WO | WO2005/011049 | 2/2005 |
| WO | WO2010/035831 | 4/2010 |

OTHER PUBLICATIONS

U.S. Appl. No. 08/136,098, filed Oct. 14, 1993.
U.S. Appl. No. 08/483,742, filed Jun. 7, 1995.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/ Wire Localizer, Namic® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.

B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With the LigaSure™ Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 94 In Biologic Effects of Nonionizing Electromagnetic Fields, CRC Press, Inc., pp. 1424-1428.
Chung et al., "Clinical Experience of Sutureless Closed Hemorrhoidectomy with LigaSure™" Diseases of the Colon & Rectum, vol. 46, No. 1, Jan. 2003.
Cosman et al., "Methods of Making Nervous System Lesions" in William RH, Rengachary SS (eds): Neurosurgery, New York: McGraw•Hill, vol. 111, (1984), pp. 2490-2499.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15:(1984), pp. 945-950.
Crawford et al., "Use of the LigaSure™ Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" 2004 Advanced Input Systems, located at: <http://www.advanced-input.com/lightkey> last visited on Feb. 10, 2005.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.

(56) References Cited

OTHER PUBLICATIONS

H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSure™ Vessel Sealing System: A Case Report" Innovations That Work, Feb. 2002.
Humphries Jr. et al., "Finite-Element Codes to Model Electrical Heating and Non•Llnear Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1,pp. 307-320.
Jarrett et al., "Use of the LigaSure™ Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSure™ Vessel Sealing System in Hemorrhoidectormy" American College of Surgeons (ACS) Clinic La Congress Poster (2000).
Johnson et al., "New Low-Profile Applicators for Local Heating of Tissues", IEEE Transactions on Biomedical Engineering, vol. BME-31, No. 1, Jan. 1984, pp. 28-37.
Johnson, "Use of the LigaSure™ Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure™ System Used in Laparoscopic 1st and 2nd Stage Orchiopexy" Innovations That Work, Nov. 2002.
K. Ogata, Modem Control Engineering, Prentice-Hall, Englewood Cliffs, N.J., 1970.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure™ Vessel Sealing System, the Seal of Confidence in General , Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Dec. 1999) "FlexStrand": product description, 1 page.
MDTECH product literature (Mar. 2000) I'D Wire: product description, 1 page.
Medtrex Brochure "The O.R. Pro 300" 1 page, Sep. 1998.
Michael Choti, "Abdominoperineal Resection with the LigaSure™ Vessel Sealing System and LigaSure™ Atlas 20 cm Open Instrument" Innovations That Work, Jun. 2003.
Muller et al., "Extended Left Hemicolectomy Using the LigaSure™ Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences•Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure™ versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure™ Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.

(56) References Cited

OTHER PUBLICATIONS

T. Seki et al., (1994) "Ultrasonically Guided Percutaneous Microwave Coagulation Therapy for Small Hepatocellular Carcinoma," Cancer 74(3):817•825.
Urologix, Inc.—Medical Professionals: Targis™ Technology (Date Unknown). "Overcoming the Challenge" located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation—'COA-COMP'" Neurosurgical Review 7:2-3 (1984) pp. 187-190.
W. Scott Helton, "LigaSure™ Vessel Sealing System: Revolutionary Hemostasis Product for General Surgery" Sales/Product Literature 1999.
Wald et aI., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 02786604.5 dated Feb. 10, 2010.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 04778192.7 dated Jul. 1, 2009.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Aug. 4, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2008.
European Search Report EP 07015601.3 dated Jan. 4, 2008.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08007924.7 partial dated Aug. 17, 2010.
European Search Report EP 08011282 dated Aug. 14, 2009.
European Search Report EP 08011705 dated Aug. 20, 2009.
European Search Report EP 08011705.4 extended dated Nov. 4, 2009.
European Search Report EP 08012829.1 dated Oct. 29, 2008.
European Search Report EP 08015842 dated Dec. 5, 2008.
European Search Report EP 08019920.1 dated Mar. 27, 2009.
European Search Report EP 08020530.5 dated May 27, 2009.
European Search Report EP 08169973.8 dated Apr. 6, 2009.
European Search Report EP 09010873.9 extended dated Nov. 13, 2009.
European Search Report EP 09010877.0 extended dated Dec. 3, 2009.
European Search Report EP 09151621 dated Jun. 18, 2009.
European Search Report EP 09156861.8 dated Aug. 4, 2009.
European Search Report EP 09161502.1 dated Sep. 2, 2009.

(56) References Cited

OTHER PUBLICATIONS

European Search Report EP 09161502.1 extended dated Oct. 30, 2009.
European Search Report EP 09165976.3 extended dated Mar. 17, 2010.
European Search Report EP 09166708 dated Oct. 15, 2009.
European Search Report EP 09166708.9 dated Mar. 18, 2010.
European Search Report EP 09169376.2 extended dated Dec. 16, 2009.
European Search Report EP 09172188.6 extended dated Apr. 23, 2010.
European Search Report EP 09172838.6 extended dated Jan. 20, 2010.
European Search Report EP 09173268.5 extended dated Jan. 27, 2010.
European Search Report EP 10001767.2 extended dated Jun. 18, 2010.
European Search Report EP 10004950.1 extended dated Jul. 2, 2010.
European Search Report EP 10004951.9 extended dated Jul. 2, 2010.
European Search Report EP 10158944.8 extended dated Jun. 21, 2010.
European Search Report EP 10161722.3 extended dated Jun. 16, 2010.
European Search Report EP 10163235.4 dated Aug. 10, 2010.
International Search Report PCT/US98/18640 dated Jan. 29, 1999.
International Search Report PCT/US98/23950 dated Jan. 14, 1999.
International Search Report PCT/US99/24869 dated Feb. 11, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2005.
International Search Report PCT/US05/36168 dated Aug. 28, 2006.
International Search Report PCT/US08/052460 dated Apr. 24, 2008.
International Search Report PCT/US09/31658 dated Mar. 11, 2009.
International Search Report PCT/US10/032796 dated Jul. 28, 2010.

* cited by examiner

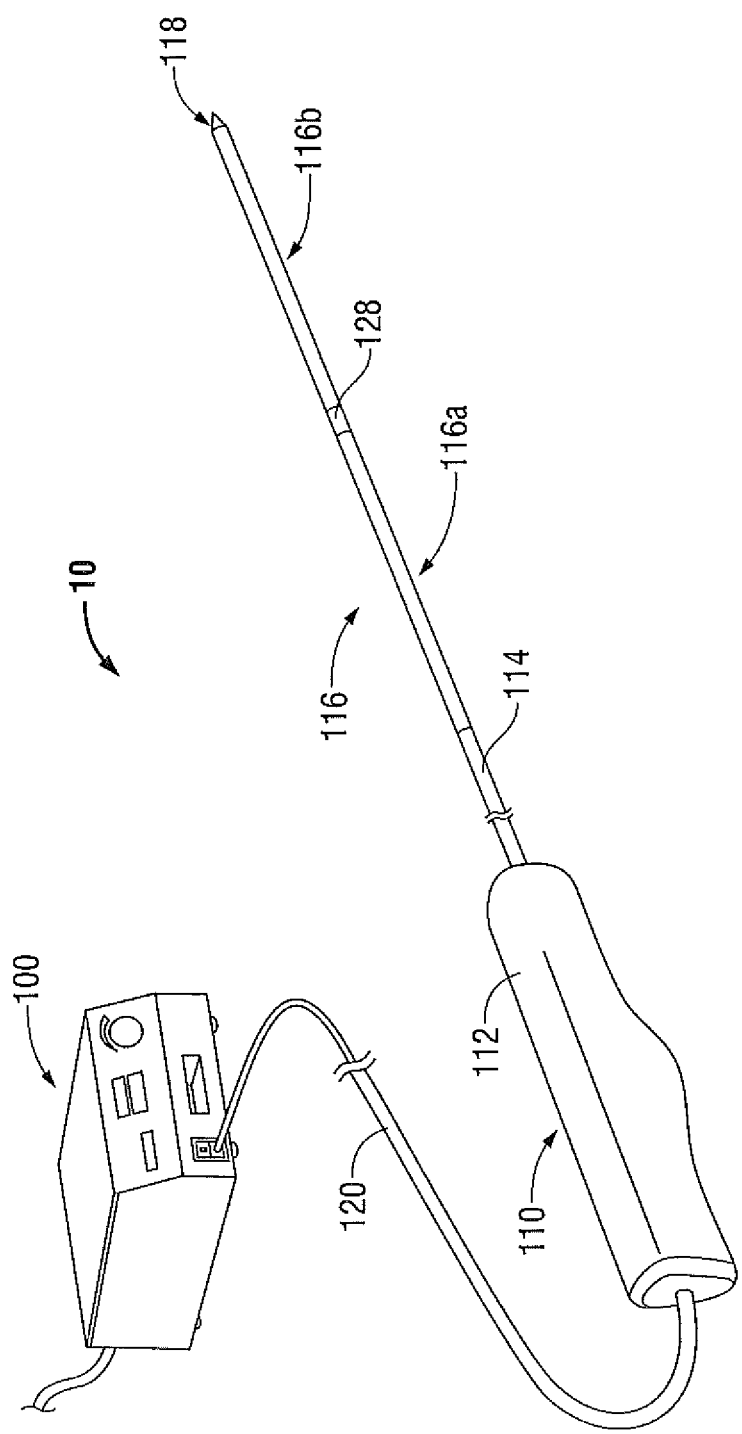

DUAL ANTENNA MICROWAVE RESECTION AND ABLATION DEVICE, SYSTEM AND METHOD OF USE

BACKGROUND

1. Technical Field

The present disclosure relates to a systems, apparatus and methods for performing a medical procedure. More particularly, the present disclosure relates to a dual antenna microwave resection and ablation device, and methods of using the same to treat tissue.

2. Description of Related Art

In the treatment of diseases such as cancer, certain types of cancer cells have been found to denature at elevated temperatures (which are slightly lower than temperatures normally injurious to healthy cells.) These types of treatments, known generally as hyperthermia therapy, typically utilize electromagnetic radiation to heat diseased cells to temperatures above 41° C., while maintaining adjacent healthy cells at lower temperatures where irreversible cell destruction will not occur. Other procedures utilizing electromagnetic radiation to heat tissue also include ablation and coagulation of the tissue. Such microwave ablation procedures, e.g., such as those performed for menorrhagia, are typically done to ablate and coagulate the targeted tissue to denature or kill the tissue. Many procedures and types of devices utilizing electromagnetic radiation therapy are known in the art. Such microwave therapy is typically used in the treatment of tissue and organs such as the prostate, heart, liver, lung, kidney, and breast.

Presently, there are several types of microwave probes in use, e.g., monopole, dipole, and helical. A monopole antenna probe consists of a single, elongated microwave conductor exposed at the end of the probe. The probe is typically surrounded by a dielectric sleeve. A dipole antenna consists of a coaxial construction having an inner conductor and an outer conductor with a dielectric junction separating a portion of the inner conductor. The inner conductor may be coupled to a portion corresponding to a first dipole radiating portion, and a portion of the outer conductor may be coupled to a second dipole radiating portion. The dipole radiating portions may be configured such that one radiating portion is located proximally of the dielectric junction, and the other portion is located distally of the dielectric junction. In the monopole and dipole antenna probes, microwave energy generally radiates perpendicularly from the axis of the conductor.

The typical microwave antenna has a long, thin inner conductor that extends along the axis of the probe and is surrounded by a dielectric material and is further surrounded by an outer conductor around the dielectric material such that the outer conductor also extends along the axis of the probe.

In the case of tissue ablation, a high radio frequency electrical current in the range of about 500 MHz to about 10 GHz is applied to a targeted tissue site to create an ablation volume, which may have a particular size and shape. The ablation volume is correlated to antenna design, antenna performance, antenna impedance and tissue impedance. The particular type of tissue ablation procedure may dictate a particular ablation volume in order to achieve a desired surgical outcome. By way of example, and without limitation, a spinal ablation procedure may call for a longer, narrower ablation volume, whereas in a prostate ablation procedure, a more spherical ablation volume may be required.

One particular ablation procedures is a tissue resection procedure. In a tissue resection procedure a clinician first determines that portion of a particular organ, containing unhealthy tissue needs to be resected or removed. A resection line is positioned on the organ, between the unhealthy tissue and the healthy tissue, such that when the tissue along the resection line is ablated, the unhealthy portion may be removed while leaving a sufficient portion of the organ in a viable or functional manor.

One step in a microwave resection or ablation procedure is the step of placing one or more microwave energy delivery device in a portion of target tissue. The placement step is a critical step because proper placement often depends on several factors including the size and shape of the desired ablation region, the type of ablation device (or devices) used, the parameters of the microwave energy signal (i.e., frequency, power, duty-cycle, etc.) and the predicted ablation size that the ablation device may generate.

The placement step becomes even more complicated when the procedure requires a plurality of ablation devices. For example, a resection procedure, which requires the ablation of tissue along a predefined resection line, often requires the placement of a plurality of microwave energy delivery devices along a particular resection line. One particular method of placement includes the insertion of a plurality of tissue penetrating microwave energy delivery devices that are positioned in the target tissue by percutaneous insertion.

In a resection procedure, once the location of the resection line has been determined, the clinician then determines an arrangement of ablation devices that will ablate the tissue along the resection line. This arrangement is typically determined by the predicted ablation region size and shape for the selected ablation device or devices. In most resection procedures a plurality of ablation devices are positioned along the resection line in order to deliver a sufficient amount of energy to achieve complete ablation of the tissue along the resection line.

In one known resection method ablation, the resection is performed by performing a first ablation along a resection line, repositioning the ablation device to a subsequent position along the resection line and performing a subsequent ablation. This step is repeated along the resection line until the entire resection line is ablated. In another resection method, a plurality of ablation devices are inserted along a resection line and the plurality of devices are simultaneously energized (or nearly simultaneously energized) to ablate the tissue along the resection line. While both methods are effective, the first method is time consuming because a plurality of ablations are performed in sequence. The second method requires precise placement of the plurality of devices to insure complete ablation with minimal interaction or interference between adjacent devices.

Regardless of the method used, resection procedures are complicated because the desired ablation region for a typical resection procedure is much different in shape and size than the desired ablation region for a typical ablation procedure. The target tissue in an ablation procedure is typically a tumorous mass that is usually circular, elliptical or oblong. As such, microwave ablation devices have typically been design to generate round, oblong or egg-shaped ablation regions. In contrast to an ablation procedure, a resection procedure typically requires ablation of an elongated region of tissue along the resection line, wherein the length of the ablation region in a resection procedure is typically much greater than the width and/or thickness of the ablation region generated by a typical ablation device.

The difference in shape of the desired ablation region becomes problematic because a clinician typically uses the same ablation device for ablation procedures and resection procedure.

SUMMARY

The present disclosure describes a dual antenna microwave resection and ablation device configured to generate ablation regions of desirable size and dimension for ablation procedures and resection procedures.

One embodiment of the present disclosure relates to a system for generating microwave energy having a microwave generator and a transmission line that connects to a dual antenna microwave device. The microwave generator generates a first and second microwave signals that are transmitted to the dual antenna microwave device by the transmission line. The dual antenna microwave device includes a first antenna, a second antenna distal of the first antenna and a dual-sided choke positioned between the first antenna and the second antenna. The first antenna receives the first microwave frequency signal from the transmission line between a first conductor and a second conductor of the transmission line and the second antenna receives the second microwave frequency signal from the second conductor and a third conductor of the transmission line. The dual-sided choke includes a choke conductor that further includes a first antenna choke circuit and a second antenna choke circuit. The first antenna choke circuit is configured to limit the propagation of electromagnetic fields generated by the first antenna toward the second antenna and the second antenna choke circuit is configured to limit the propagation of electromagnetic fields generated by the second antenna toward the first antenna. In one embodiment the choke conductor electrically connects to the second conductor.

The length of the first antenna, the second antenna and/or the dual-sided choke may be related to one-quarter wavelength of the first microwave frequency signal and/or the second microwave frequency signal. The first antenna and the second antenna may be configured to simultaneously radiate the first and second microwave frequency signals, respectively. A dielectric coating may be disposed at least partially over the first antenna, the second antenna and/or the dual-sided choke.

The first antenna may further include a distal radiating section and the second antenna may further include a proximal radiating section, wherein the first antenna and the second antenna generate electromagnetic fields between the distal radiating section of the first antenna and the proximal radiating section of the second antenna. The proximal radiating section and the distal radiating section may have a length proportional to an effective wavelength of the radiation transmitted by the antenna assembly.

In a further embodiment, the dual antenna microwave device further includes a feedline having an inner conductor, an outer conductor and a triaxial conductor. At least a portion of the feedline includes the inner conductor, the outer conductor and the triaxial conductor in a triaxial orientation.

The first antenna may further include a first feedpoint and the second antenna may further include a second feedpoint. The distance between the midpoint of the first feedpoint and the midpoint of the second feedpoint may be related to a quarter wavelength of at least one of the first and second microwave frequency signals.

In a further embodiment, the first antenna choke circuit and/or the length of the second antenna choke circuit may be related to a quarter wavelength of the first microwave frequency signal and/or the second microwave frequency signal.

Another embodiment of the present disclosure is a device for ablating tissue, including a transmission line, a first antenna, a second antenna and a dual-sided choke. The second antenna is distal the first antenna and the dual-sided choke is positioned between the first antenna and the second antenna. The transmission line connects the device to a microwave energy source and transmits a first and a second microwave frequency signal from the microwave energy source to the first and second antennas. The first antenna receives the first microwave frequency signal between a first conductor and a second conductor of the transmission line and the second antenna receives the second microwave frequency signal between the second conductor and a third conductor of the transmission line. The dual-sided choke includes a choke conductor that further includes a first antenna choke circuit and a second antenna choke circuit. The first antenna choke circuit is configured to limit the propagation of electromagnetic fields generated by the first antenna toward the second antenna and the second antenna choke circuit is configured to limit the propagation of electromagnetic fields generated by the second antenna toward the first antenna.

Yet another embodiment of the present disclosure relates to a microwave antenna assembly for applying microwave energy therapy, including a proximal portion having an inner conductor, an outer conductor and a triaxial conductor each extending therethrough. The assembly also includes a first antenna, a second antenna and a dual-sided choke. In the proximal portion the inner conductor is disposed within the outer conductor and the outer conductor is disposed within the triaxial conductor. The first antenna includes a first antenna distal radiating section that connects to the triaxial conductor and a first antenna proximal radiating section that connects to the outer conductor. The second antenna includes a second antenna distal radiating section that connects to the inner conductor and a second antenna proximal radiating section that connects to the inner conductor. The dual-sided choke, having at least a portion therewith disposed between the first antenna and the second antenna, includes a first antenna choke circuit and a second antenna choke circuit. The first antenna choke circuit is configured to limit the propagation of electromagnetic fields generated by the first antenna toward the second antenna and the second antenna choke circuit is configured to limit the propagation of electromagnetic fields generated by the second antenna toward the first antenna

BRIEF DESCRIPTION OF THE DRAWINGS

FIG. 1A is a schematically-illustrated view of a microwave energy delivery system including a dual antenna microwave resection and ablation device (DAMRAD) in accordance with one embodiment of the present disclosure;

DETAILED DESCRIPTION

Figure 1B:
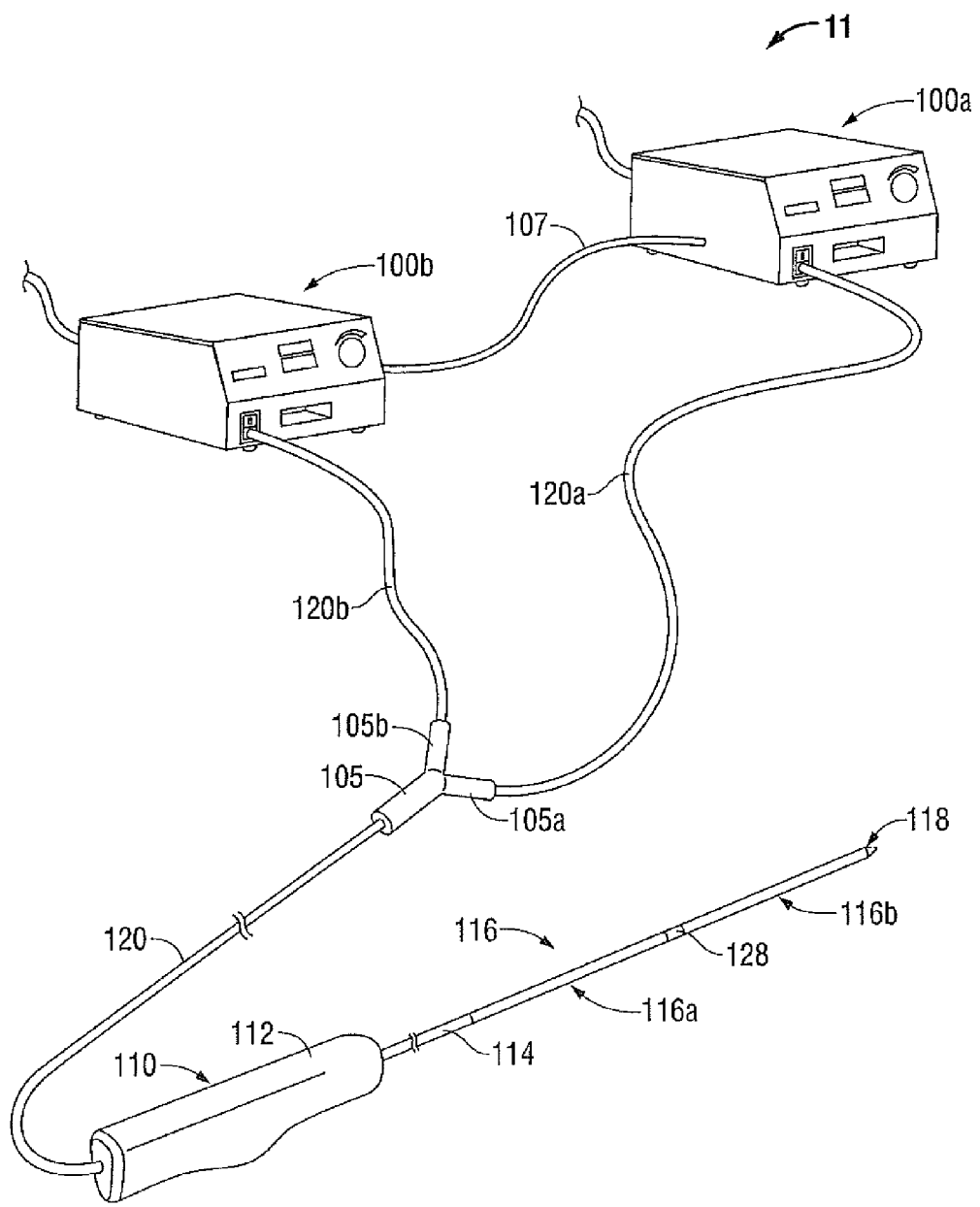
FIG. 1B is a schematically-illustrated view of a microwave energy delivery system including first and second microwave signal generators that provide first and second microwave energy signals to a DAMRAD in accordance with another embodiment of the present disclosure.

Detailed embodiments of the present disclosure are described herein; however, it is to be understood that the disclosed embodiments are merely examples and may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Referring to FIG. 1A, a microwave energy delivery system 10 is shown including a microwave generator 100, a dual antenna microwave resection and ablation device (DAMRAD) 110 employing embodiments of the present disclosure and a triaxial transmission cable 120 connected therebetween. Triaxial transmission cable 120 may be permanently affixed to the DAMRAD 110 (as illustrated in FIG. 1A) or triaxial transmission cable 120 may be separate from the DAMRAD 110. Alternatively, DAMRAD 110 may connect to a plurality of coaxial transmission cables (not explicitly shown) each of the plurality of coaxial transmission cables providing a microwave energy signal to the DAMRAD 110. The microwave energy signals provided to the triaxial transmission cable 120 or to the plurality of coaxial transmission cables may be in-phase or out-of-phase with respect to each other. In one embodiment, the microwave generator 100 may further include a microwave signal splitter (not explicitly shown) configured to divide a single microwave energy signal, generated by the microwave generator 100, into two signals for the DAMRAD 110.

As illustrated in FIG. 1A, DAMRAD 110 includes a percutaneous device having a sharpened tip 118 configured to penetrate tissue. The antenna portion 116 includes a proximal antenna 116a and a distal antenna 116b separated by a dual-sided choke 128. The handle 112 is connected to the antenna portion 116 by an elongated shaft 114.

Elongated shaft 114 is configured to provide a microwave energy signal to the proximal and distal antennas 116a, 116b respectively. In one embodiment the elongated shaft 114 includes three conductors arranged in a triaxial configuration thereby forming a triaxial transmission line. Alternatively, elongated shaft 114 may include a plurality of transmission lines each supplying a microwave energy signal to one of the antennas 116a, 116b.

Microwave generator 100 is configured to provide suitable microwave energy signals to the DAMRAD 110. The microwave energy signals may be substantially identical or may be related in one or more ways (e.g., in-phase, similar frequency and/or power level). For example, microwave generator 100 may include a phase-shifting circuit (not explicitly shown) configured to offset the first and second microwave signals at a predetermined microwave frequency by a selected phase shift. The selected phase shift may be determined by the clinician, by a physical property or configuration of the DAMRAD 116 or may be selected based on feedback (i.e., reflected energy) measured by the microwave generator 100.

Microwave generator may also include first and second microwave signal generating circuits (not explicitly shown) that generate a first microwave signal at a first frequency and a second microwave signal at a second frequency, wherein the first and second frequencies are not the same. In one embodiment, the first and second frequencies are harmonics.

Referring to FIG. 1B, a microwave energy delivery system 11 is shown including a first microwave generator 100a and a second microwave generator 100b connected to a DAMRAD 100 through a coaxial-to-triaxial connector 105. First microwave generator 100a generates a first microwave energy signal and second microwave generator 100b generates a second microwave signal. The first and second microwave signals are provided to the coaxial-to-triaxial connector 105 through first and second coaxial cables 120a, 120b, respectively, connected to the first and second coaxial connectors 105a, 105b. Triaxial connector 105 passes the first and second microwave energy signals to the triaxial cable 120 connected to the DAMRAD 100. First and second microwave generators 100a, 100b may connect to each other through a microwave generator interface cable 107 and provide control and/or synchronization information therebetween.

The first and second microwave signals generated by the first and second microwave generators 100a, 100b may be substantially identical or may be related in one or more ways (e.g., in-phase, similar frequency and/or power level). For example, first microwave signal generated by first microwave generator 100a may be shifted in phase with respect to the second microwave signal generated by second microwave generator 100b. Microwave generator interface cable 107 may provide one or more parameters related to one of the first or second microwave signals. For example, microwave generator interface cable 107 may provide signal phase data, a timing signal or frequency data between the first and second generators 100a, 100b. Microwave interface cable 107 may provide a sample of, or signal related to, one of the first and/or second microwave signals.

The phase shift between the first and the second microwave signals may be determined by the clinician, by a physical property or configuration of the DAMRAD 116 or may be selected based on feedback (i.e., reflected energy) measured by the microwave generator 100.

The DAMRAD may be designed to operate at microwave frequencies of 915 MHz, 2.45 GHz or any other suitable frequency. A DAMRAD designed to operate at 915 MHz, as compared to a DAMRAD designed to operate at 2.45 GHz, would include longer antenna lengths (due to the longer wavelength) and therefore would produce longer ablation regions, as described hereinbelow.

Figure 2:
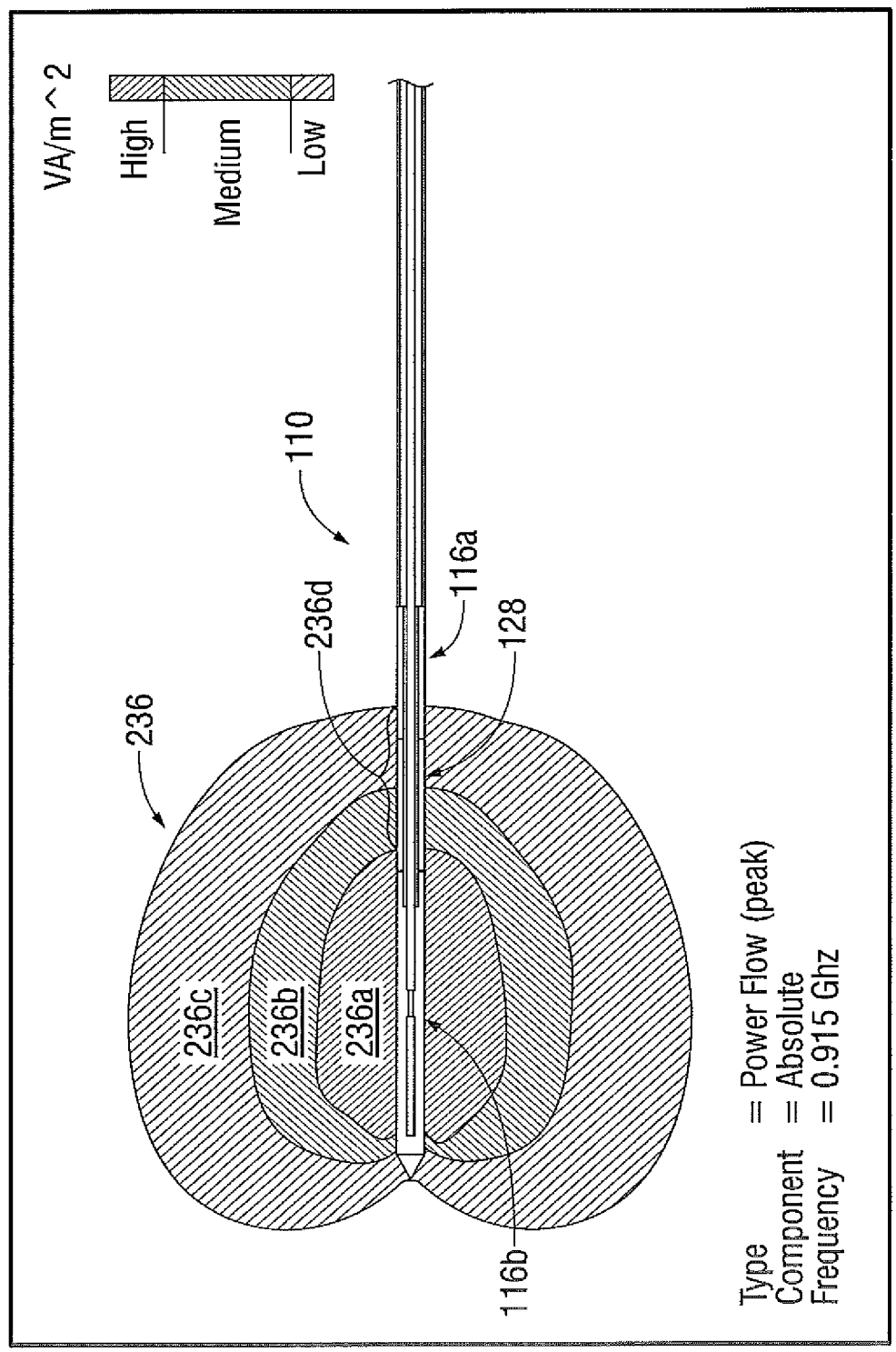
FIG. 2 is a graphical illustration of a simulated power flow generated by the distal antenna of the DAMRAD.
Figure 3:
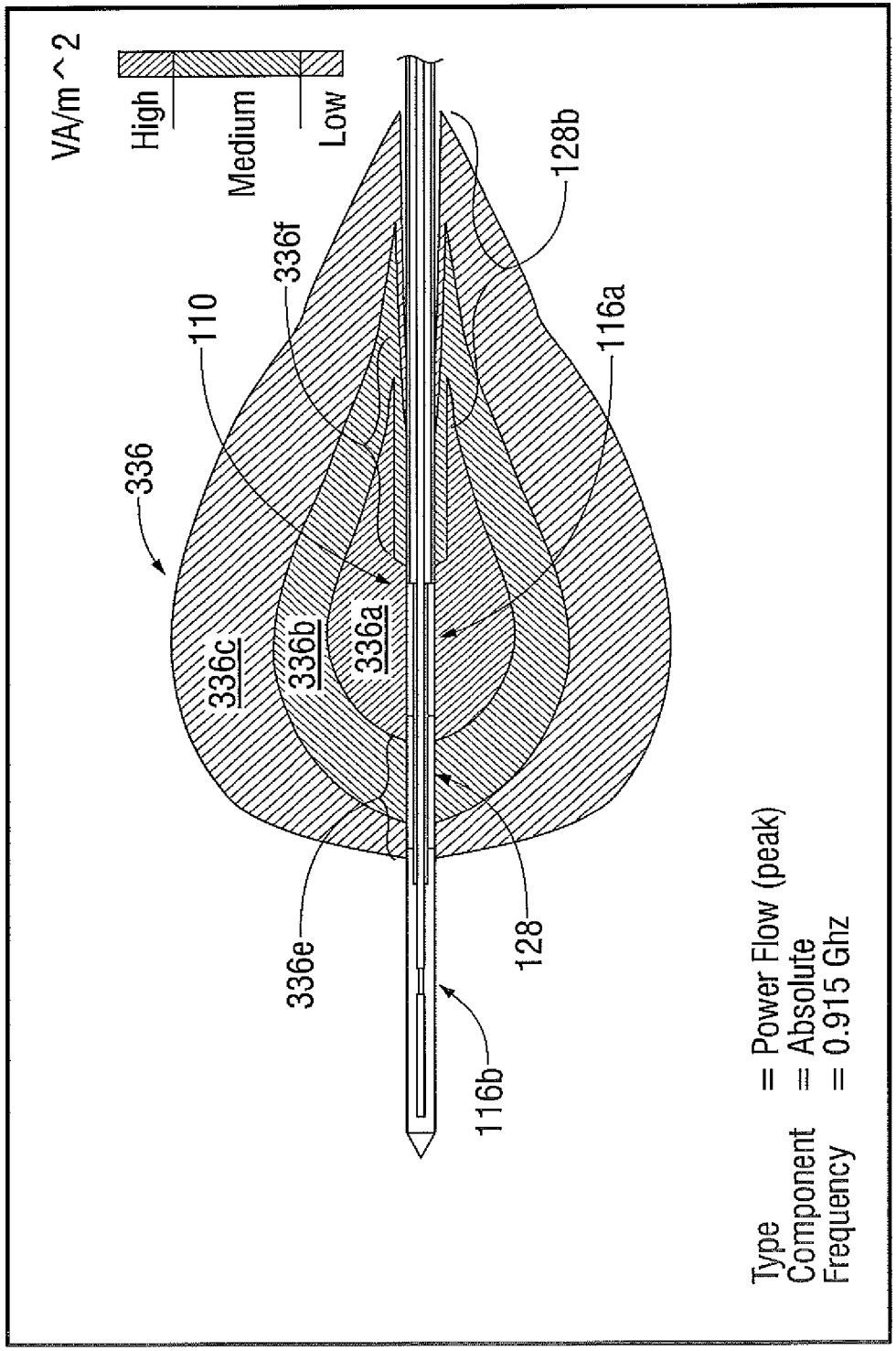
FIG. 3 is a graphical illustration of a simulated power flow generated by the proximal antenna of the DAMRAD.
Figure 4:
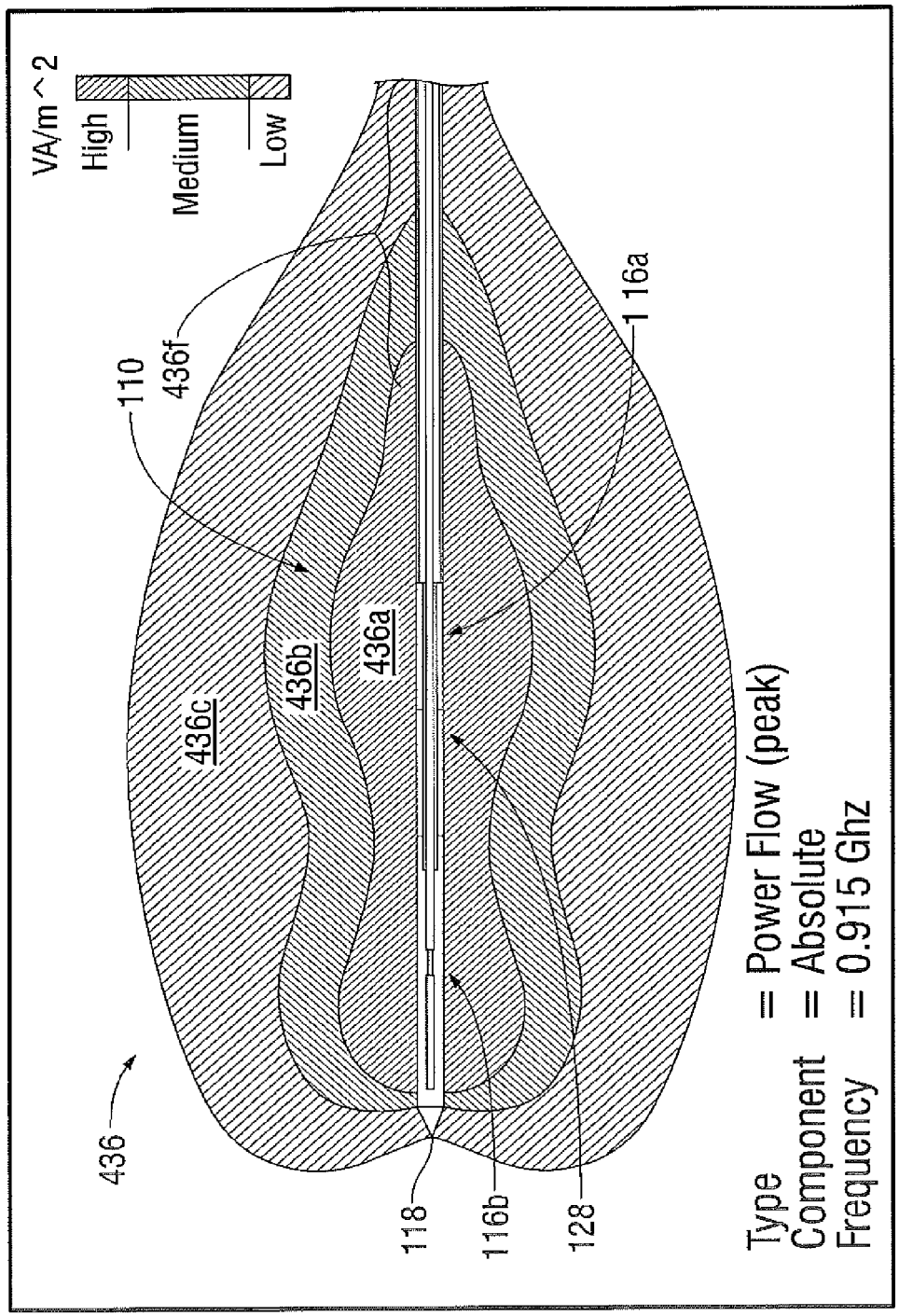
FIG. 4 is a graphical illustration of a simulated power flow generated by the distal and proximal antennas of the DAMRAD.

The energy associated with fields generated by a microwave antenna may be represented as electric field strengths (hereinafter, E-field) or by magnetic field strengths (hereinafter, H-field), wherein each provide equally valid expressions of radiant energy flow. The simulated power flows 236, 336, 436 in FIGS. 2-4 illustrates power flow as the product of the E-field (in V/m) and H-field (in A/m) wherein the units of the product of the E-field and the H-field yields $VA/m^2$. The simulations in FIGS. 2-4 were performed with a 0.915 GHz microwave energy signal provided to the distal antenna 116b in FIG. 2, the proximal antenna 116a in FIG. 3 and the proximal and distal antennas 116a, 116b in FIG. 4.

The simulated power flows 236, 336, 436, for simplicity, are illustrated as three distinct areas of power flow. For example, as illustrated in FIG. 2 the simulated power flow 236 includes an area of high density power flow 236a, an area of medium density power flow 236b and an area of low density power flow 236c. It is understood that an actual and/or simulated power flow 236, 336, 436 may include a power flow gradient with the absolute magnitude of the power flow 236 being proportionally decreasing (linearly, non-linearly or exponentially) and related to the distance from the distal antenna 116b.

FIG. 2 is a graphical illustration of a simulated power flow 236 generated by the distal antenna 116b of the DAMRAD 110 (for illustrative purpose the DAMRAD 110 is superimposed on the graphical illustration). The DAMRAD 110 includes a distal antenna 116b a proximal antenna 116a separated by a dual-sided choke 128. The simulation was performed with a 915 MHz microwave energy signal provided to the distal antenna 216b. The proximal portion 236d of the power flow 236 is shunted by the distal side of the dual-sided choke 128 as discussed hereinbelow.

FIG. 3 is a graphical illustration of a simulated power flow 336 generated by the proximal antenna 116a of the DAMRAD 110 (for illustrative purposes the DAMRAD 110 is superimposed on the graphical illustration). For simplicity, the simulated power flow 336 is illustrated to include an area of high density power flow 336a, an area of medium density power flow 336b and an area of low density power flow 336c. The distal portion 336e of the power flow 336 is shunted by a proximal side of the dual-sided choke 128 as discussed hereinbelow. Since the proximal side of the proximal antenna 116a is unchoked, the proximal portion 336f of the power flow 336 extends beyond the proximal end of the proximal antenna 116a.

FIG. 4 is a graphical illustration of a simulation of the combined power flow 436 generated by the distal and proximal antennas 116b, 116a of the DAMRAD 110 (for illustrative purposes the DAMRAD 110 is superimposed on the graphical illustration). The simulated power flow 436 includes an area of high density power flow 436a, an area of medium density power flow 436b and an area of low density power flow 436c. The dual-sided choke 128 shunts the magnetic fields generated on the proximal portion of the distal antenna 116b and shunts the magnetic fields generated on the distal portion of the proximal antenna 116a. As such, there is little interaction between the magnetic fields generated by either antenna 116a, 116b in the area adjacent the dual-sided choke 128. Since the proximal side of the proximal antenna 116a is unchoked, the proximal portion 436f of the power flow 436 extends beyond the proximal end of the proximal antenna 116a.

The area adjacent and/or surrounding the dual-sided choke 128 of the DAMRAD 110 receives energy from the electromagnetic fields generated by the distal antenna 116b and from electromagnetic fields generated by the proximal antenna 116a thereby creating a synergistic heating effect in this region. It can be ascertained from the simulated power flows 236, 336, 436 illustrated in FIGS. 2-4 that the DAMRAD 110 is configured to generate an elongated region of high density power flow 436a that extends from the distal tip 118 of the DAMRAD 110 to a point proximal the proximal antenna 116a. As such the effective length of the ablation region that may be generated from the DAMRAD 110 is at least two times and up to three times the length of an ablation region generated from a microwave energy delivery device including a single antenna.

A synergistic heating effect in the region surround the dual-sided choke 128 may be obtained by either simultaneous energy delivery to the dual antennas 116a, 116b or by alternating the delivery of the microwave energy signal between the proximal antenna 116a and the distal antenna 116b or any combination thereof. As will be discussed hereinbelow and illustrated in FIG. 1, in at least one embodiment the microwave signals provided to the proximal antenna 116a and the distal antenna 116b are provided from the same microwave generator 100 and the triaxial transmission cable 120. As such, the microwave signals provided to the proximal antenna 116a and the distal antenna 116b share substantially identical supply paths and distances. As such, the microwave energy signals provided to the two antennas 116a, 116b are inherently in-phase with respect to each other.

As illustrated in FIGS. 2-4, the DAMRAD 110 is configured to generate ablation regions of varying sizes and shapes. The DAMRAD 110 may be utilized in a manner similar to that of a standard ablation device by utilizing and energizing only one of the dipole antennas 116a, 116b. Alternatively, in another embodiment the distal antenna 116b may be utilized to generate a typical ablation region and the proximal antenna 116a may be utilized to selectively ablate at least a portion of the insertion path. Finally, as illustrated in FIG. 4, the DAMRAD 110 is configured to generate elongated ablation region with a shape that is particularly suited for resection procedures.

Figure 5:
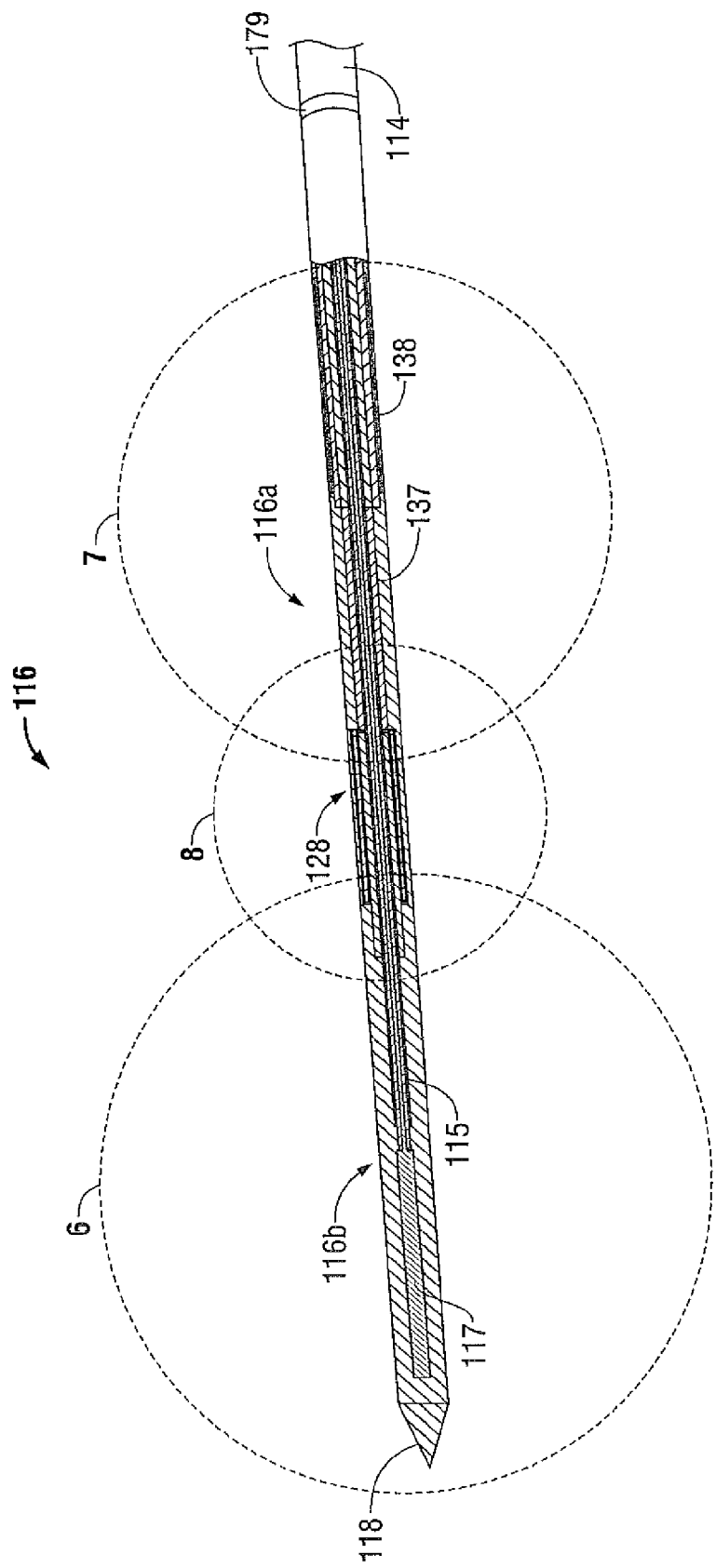
FIG. 5 is a cross-sectional illustration of the antenna portion of the DAMRAD.

FIG. 5 is a cross-sectional illustration of the antenna portion 116 of the DAMRAD 110 of FIG. 1. The antenna portion 116 includes the proximal antenna 116a, the distal antenna 116b separated by the dual-sided choke 128. Distal the distal antenna 116b is the sharpened tip 118 configured to facilitate percutaneous insertion of the DAMRAD 110 into patient tissue (not explicitly shown). The distal antenna 116b, the proximal antenna 116a and the dual-sided choke 128 are further illustrated in FIG. 6, FIG. 7 and FIG. 8, respectively, and are described in detail hereinbelow.

Figure 6:
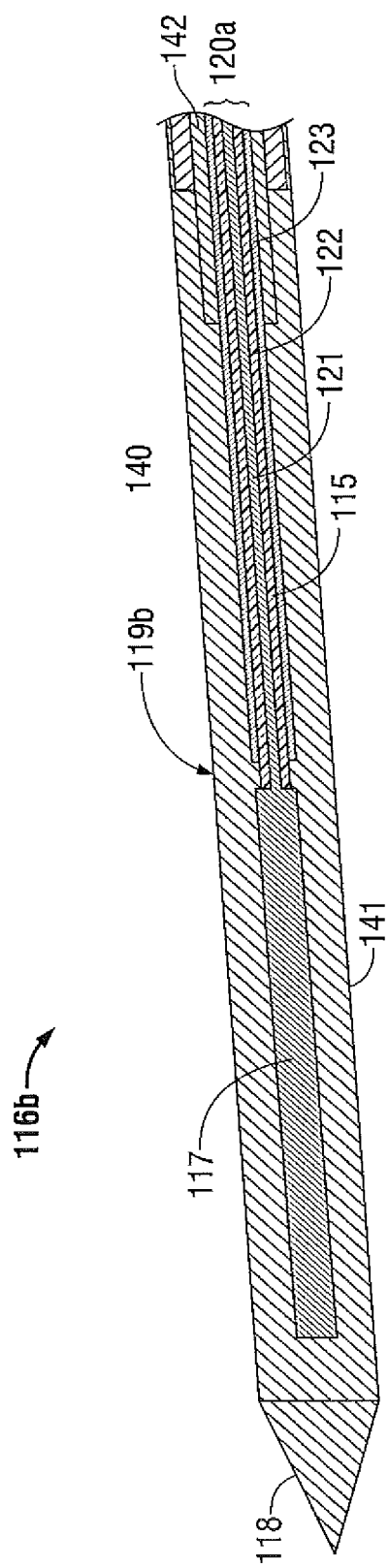
FIG. 6 is a cross-sectional illustration of the distal antenna of the DAMRAD.

FIG. 6 is a cross-sectional illustration of the distal antenna 116b of the DAMRAD 110 of FIG. 5. The distal antenna 116b is configured as a dipole antenna and includes a distal antenna distal radiating section 117 and a distal antenna proximal radiating section 115, both of which receive a microwave energy signal from the distal antenna feedpoint 119b at the distal end of the internal coaxial cable 120a. The internal coaxial cable 120a includes an inner conductor 121 and an outer conductor 123 in a coaxial arrangement and separated by an inner dielectric 122 and provides the microwave energy signal to the distal antenna feedpoint 119b.

Distal antenna 116b may be at least partially surrounded by a dielectric load sleeve 141. Dielectric load sleeve 141 insulates the various portions of the distal antenna 116b from the surrounding tissue (not explicitly shown) and is configured to provide a uniform diameter between the distal antenna 116b and the remaining portion of the DAMRAD 110. Dielectric load sleeve 141 may also provide a buffer (i.e., a dielectric buffer) between the distal antenna 116b and the changing load of the surrounding tissue (not explicitly shown). Distal antenna 116b may be inserted into the Dielectric load sleeve 141 or dielectric load sleeve 141 may be formed around the distal antenna 116b by various methods such as injection or by a shrink wrap method commonly used in the art.

Figure 7:
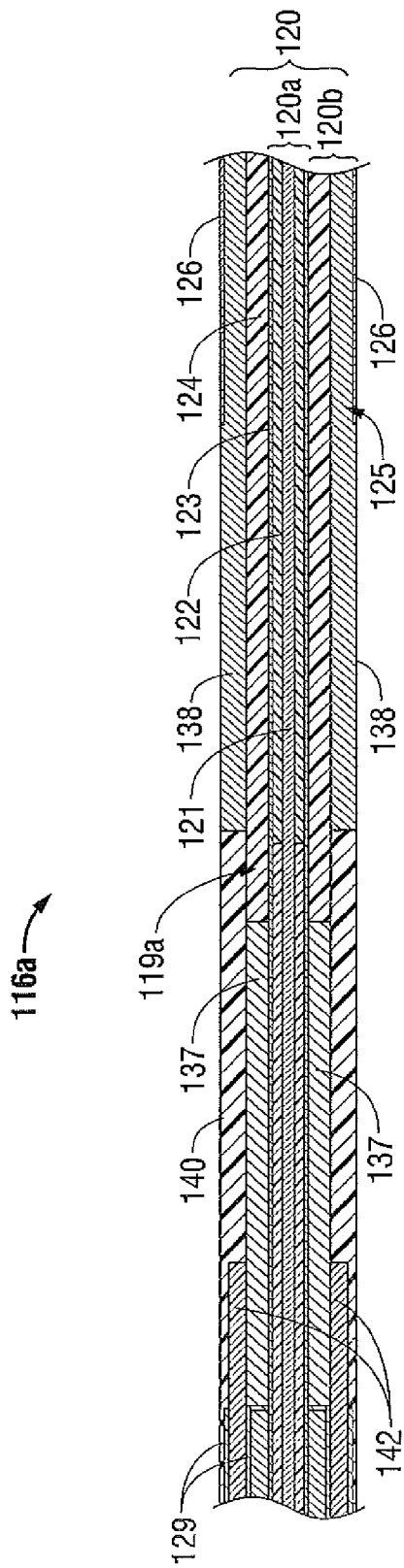
FIG. 7 is a cross-sectional illustration of the proximal antenna of the DAMRAD.

FIG. 7 is a cross-sectional illustration of the proximal antenna 116a of the DAMRAD 110 of FIG. 5. The proximal antenna 116a is configured as a dipole antenna and includes a proximal antenna distal radiating section 137 and a proximal antenna proximal radiating section 138, both of which receive a microwave energy signal from the proximal antenna feedpoint 119a at the distal end of the external coaxial cable 120b. The external coaxial cable 120b of the triaxial transmission cable 120 includes the outer conductor 123 and the triaxial conductor 125 in a coaxial arrangement and separated by an outer dielectric 124. The external coaxial cable 120b provides the microwave energy signal to the proximal antenna feedpoint 119a.

With reference to FIGS. 6 and 7, the outer conductor 123, 123 is common to the internal coaxial cable 120a and to the external coaxial cable 120b. Proximal of the proximal antenna 116a the inner conductor 121, the outer conductor 123 and the triaxial conductor 125 are in a triaxial arrangement. The inner conductor 121 and outer conductor 123 are separated by the inner dielectric 122 and the outer conductor 123 and the triaxial conductor 125 are separated by the outer dielectric 124 and together form the triaxial transmission cable 120.

The triaxial transmission cable 120 supplies a microwave energy signal to the proximal antenna 116a and to the distal antenna 116b. The triaxial transmission cable 120 configuration ensures that the feedline distance (e.g., the physical cable distance between the microwave generator 100 of FIG. 1 and the proximal antenna feedpoint 119a of FIG. 7) is the same for both microwave signals. As such, the microwave signals provided by the internal conductor 120a and the external conductor 120b are subject to substantially identical phase shifts caused by the length of the transmission line of the microwave signals.

With reference to FIGS. 5-7, the distal antenna proximal radiating section 115 and the proximal antenna distal radiating section 137 connect to the outer conductor 123 of the triaxial feedline 120. With reference to FIGS. 6 and 7, the proximal antenna feedpoint 119a and the distal antenna feedpoint 119b are offset by a distance, wherein the distance between the feedpoints 119a, 119b is related to the wavelength of the predetermined microwave frequency, or a fractional portion thereof (i.e., ¼ wavelength, ½ wavelength). The distance may be optimized and/or configured such that the DAMRAD 110 achieves long narrow ablation regions.

As illustrated in FIG. 5, a ferrite ring 179 may also be positioned on the elongated shaft 114 proximal the proximal antenna 116a to limit the intensity of the microwave energy proximal the proximal antenna 116a. Ferrite ring 179 may be constructed of any suitable metal or conductible material capable of shunting electromagnetic energy radiating proximally from the antenna 116. Ferrite ring 179 may also be constructed as a Faraday shield and may be configured to shunt electromagnetic energy radiating proximally from the antenna at the predetermined microwave frequency.

Returning to FIG. 7, the distal radiating section of the proximal antenna 137 is at least partially surrounded by a proximal dielectric load sleeve 140. Proximal dielectric load sleeve 140 may be connected to, or be part of, the outer jacket 126, the distal dielectric load sleeve 141 (see FIG. 6) or both.

Figure 8:
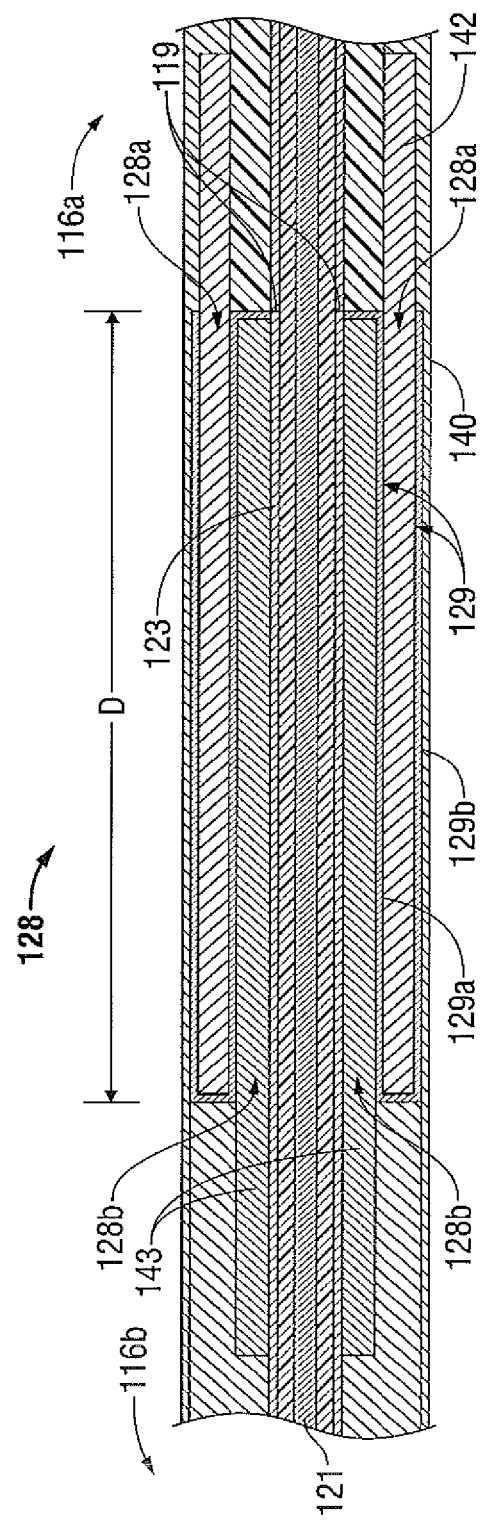
FIG. 8 is a cross-sectional illustration of the dual-sided choke of the DAMRAD in accordance with another embodiment of the present disclosure

FIG. 8 is a cross-sectional illustration of the dual-sided choke 128 of the DAMRAD 110 of FIG. 1 in accordance with another embodiment of the present disclosure. The dual-sided choke 128 includes a choke conductor 129 electrically connected to the outer conductor 123. In one embodiment, at least a portion of the choke conductor 129 partially surrounds a portion of the proximal antenna choke extended dielectric 142 and/or the distal antenna choke extended dielectric 143. The distal antenna choke circuit 128b is formed between the outer conductor 123 and the first segment 129a of the choke conductor 129, with the opening of the distal antenna choke circuit 128b being directed toward the distal antenna 116b. The proximal antenna choke circuit 128a is formed between the first segment 129a and the second segment 129b of the choke conductor 129, wherein the opening of the proximal antenna choke circuit 128a is directed toward the proximal antenna 116a. At the dual-sided choke termination point 119, the choke conductor 129 connects to the outer conductor 123 and forms a suitable electrical connection. Electrical connection may be a solder connection, a weld, a press-fit connection or any other suitable connection. The outer surface of the dual-sided choke 128 is coated with the dielectric load sleeve 140 that may be connected to, or formed from, an outer jacket (see FIG. 7, outer jacket 127) a distal dielectric load sleeve (see FIG. 6, dielectric load sleeve 141) or both. Dual-sided choke 128 may be used in conjunction with a ferrite ring (see FIG. 5, ferrite ring 179 positioned on the elongated shaft 114 proximal the proximal antenna 116a).

The proximal antenna choke circuit 128a and the distal antenna choke circuit 128b may be configured as quarter-wave, shorted chokes and may aid in limiting the intensification of the microwave energy beyond the antennas 116a, 116b.

Figure 9:
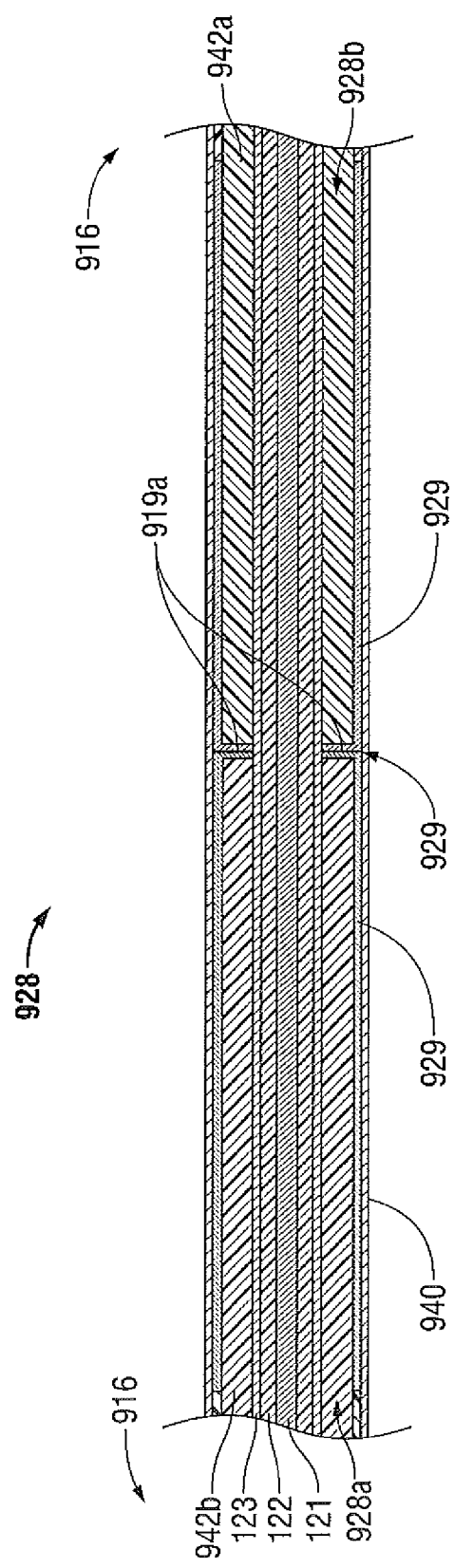
FIG. 9 is a cross-sectional illustration of a double-sided choke of the DAMRAD in accordance with yet another embodiment of the present disclosure.

In another embodiment, the dual-sided choke 128 of FIG. 8 may be replaced with a double-sided choke 928, as illustrated in FIG. 9. Double-sided choke 928 includes a proximal antenna choke circuit 928a and a distal antenna choke circuit 928b. The proximal antenna choke circuit 928a includes a proximal choke segment 929a that electrically connects to the outer conductor 123 through the common choke conductor 929. Proximal antenna choke circuit 928a may at least partially surround the proximal antenna choke extended dielectric 942. The distal antenna choke circuit 928b includes a distal choke segment 929b that electrically connects to the outer conductor 123 through the common choke conductor 929. Distal antenna choke circuit 928b may at least partially surround the distal antenna choke extended dielectric 943. As illustrated in FIG. 9, the proximal antenna choke circuit 928a and the distal antenna choke circuit 928b both connect to the outer conductor through the common choke conductor 929. In another embodiment, individual connections to the outer conductor 123 may be provided for each choke circuit 928a, 928b. The outer surface of the double-sided choke 928 is coated with the dielectric load sleeve 940 that may be connected to, or formed from, the outer jacket (see FIG. 7, outer jacket 126), the distal dielectric load sleeve (see FIG. 6, distal dielectric load sleeve 141) or both. Double-sided choke 928 may be used in conjunction with a ferrite ring (see FIG. 5, ferrite ring 179 positioned on the elongated shaft 114 proximal the proximal antenna 116a).

With reference to FIGS. 8 and 9, the longitudinal length of the dual-sided choke 128 is less than the longitudinal length of the double-sided chokes 928. As such, spacing between the proximal antenna 116a, 916a and the distal antenna 116b, 916b on a device with a dual-sided choke 128 and a dual-sided choke 928, respectively, is different. The spacing between the proximal antenna 116a, 916a and the distal antenna 116b, 916b affects the phase relationship between the microwave energy radiated from the proximal antenna 116a, 916a and distal antennas 116b, 916b. As such, a device with a dual-sided choke 128 provides a ifferent phase relationship between the microwave energy radiated from the proximal antenna 116a and the distal antenna 116b than a device with a double-sided choke 928.

With continued reference to FIGS. 8 and 9, a device with a double-sided choke 928 may provide a reduction in the overall diameter of the antenna 916 since a dual-sided choke configuration positions one choke radially outward from the other choke while the double-sided choke 928 positions the chokes 928a, 928b on substantially identical radial planes.

As various changes could be made in the above constructions without departing from the scope of the disclosure, it is intended that all matter contained in the above description shall be interpreted as illustrative and not in a limiting sense. It will be seen that several objects of the disclosure are achieved and other advantageous results attained, as defined by the scope of the following claims.

What is claimed is:

1. An electrsurgical system for generating microwave energy, the system comprising:
    a microwave generator configured to generate a first microwave frequency signal and a second microwave signal;
    a transmission line configured to transmit the first and the second microwave frequency signals;
    a dual antenna microwave device including:
        a first antenna configured to receive the first microwave frequency signal from the transmission line between a first conductor and a second conductor;
        a second antenna, distal of the first antenna, configured to receive the second microwave frequency signal from the transmission line between the second conductor and a third conductor; and
        a dual-sided choke, positioned between the first antenna and the second antenna, the dual-sided choke including a choke conductor including a first antenna choke circuit and a second antenna choke circuit,
    wherein the first antenna choke circuit is configured to limit the propagation of electromagnetic fields generated by the first antenna toward the second antenna and the second antenna choke circuit is configured to limit the propagation of electromagnetic fields generated by the second antenna toward the first antenna.

2. The system according to claim 1, wherein the choke conductor electrically connects to the second conductor.

3. The system according to claim 1, wherein the length of at least one of the first antenna, the second antenna and the dual-sided choke is related to one-quarter wavelength of one of the first microwave frequency signal and the second microwave frequency signal.

4. The system according to claim 1, wherein the first antenna and the second antenna are configured to simultaneously radiate the first and second microwave frequency signals, respectively.

5. The system according to claim 1, further including a dielectric coating disposed at least partially over at least one of the first antenna, the second antenna and the dual-sided choke.

6. The system according to claim 1, wherein the first antenna further includes a distal radiating section and the second antenna further includes a proximal radiating section, wherein the distal radiating section and the proximal radiating section are configured to radiate microwave energy between the distal end of the first antenna and the proximal end of the second antenna.

7. The system according to claim 6, wherein the proximal radiating section and the distal radiating section have a length proportional to an effective wavelength of the radiation transmitted by the antenna assembly.

8. The system according to claim 1, where in the dual antenna microwave device further includes:
    a feedline including:
        an inner conductor forming the first conductor,
        an outer conductor forming the second conductor, and
        a triaxial conductor forming the third conductor,
    wherein at least a portion of the feedline includes the inner conductor, the outer conductor and the triaxial conductor in a triaxial orientation.

9. The system according to claim 1, wherein the first antenna includes a first feedpoint and the second antenna includes a second feedpoint, wherein the distance between the midpoint of the first feedpoint and the midpoint of the second feedpoint is related to a quarter wavelength of at least one of the first and second microwave frequency signals.

10. The system according to claim 1, wherein at least one of the length of the first antenna choke circuit and the length of the second antenna choke circuit is related to a quarter wavelength of at least one of the first microwave frequency signal and the second microwave frequency signal.

11. A device for ablating tissue, comprising:
    a first antenna configured to receive a first microwave frequency signal between a first conductor and a second conductor;
    a second antenna, distal of the first antenna, configured to receive a second microwave frequency signal from between the second conductor and a third conductor; and
    a dual-sided choke, positioned between the first antenna and the second antenna the dual-sided choke including:
        a choke conductor including a first antenna choke circuit and a second antenna choke circuit,
    wherein the first antenna choke circuit is configured to limit the propagation of electromagnetic fields generated by the first antenna toward the second antenna and the second antenna choke circuit is configured to limit the propagation of electromagnetic fields generated by the second antenna toward the first antenna.

12. The device according to claim 11, wherein the choke conductor electrically connects to the second conductor.

13. The device according to claim 11, wherein the length of at least one of the first antenna, the second antenna and the dual-sided choke is related to one-quarter wavelength of one of the first microwave frequency signal and the second microwave frequency signal.

14. The device according to claim 11, wherein the first antenna and the second antenna are configured to simultaneously radiate the first and second microwave frequency signals, respectively.

15. The device according to claim 11, further including a dielectric coating disposed at least partially over at least one of the first antenna, the second antenna and the dual-sided choke.

16. The device according to claim 11, wherein the first antenna further includes a distal radiating section and the second antenna further includes a proximal radiating section, wherein the distal radiating section and the proximal radiating section are configured to radiate microwave energy between the distal end of the first antenna and the proximal end of the second antenna.

17. The device according to claim 16, wherein the proximal radiating section and the distal radiating section have a length proportional to the effective wavelength of one of the first microwave frequency signal and the second microwave frequency signal.

18. The device according to claim 11, wherein the first conductor, the second conductor and the third conductor of the transmission line are disposed in a triaxial orientation.

19. The device according to claim 11, wherein the first antenna includes a first feedpoint and the second antenna includes a second feedpoint, wherein the distance between the midpoint of the first feedpoint and the midpoint of the second feedpoint is related to a quarter wavelength of at least one of the first and second microwave frequency signals.

20. The device according to claim 11, wherein at least one of the length of the first antenna choke circuit and the length of the second antenna choke circuit is related to a quarter wavelength of at least one of the first microwave frequency signal and the second microwave frequency signal.

21. A microwave antenna assembly for applying microwave energy therapy, comprising:

a proximal portion having an inner conductor, an outer conductor and a triaxial conductor each extending therethrough, the inner conductor disposed within the outer conductor and the outer conductor disposed within the triaxial conductor;

a first antenna including a first antenna distal radiating section and a first antenna proximal radiating section, the first antenna proximal radiating section connected to the triaxial conductor and the first antenna distal radiating section connected to the outer conductor;

a second antenna including a second antenna distal radiating section and a second antenna proximal radiating section, the second antenna proximal radiation section connected to the outer conductor and the second antenna distal radiating section connected to the inner conductor;

a dual-sided choke having at least a portion therewith disposed between the first antenna and the second antenna, the dual-sided choke including a first antenna choke circuit and a second antenna choke circuit, wherein the first antenna choke circuit is configured to limit the propagation of electromagnetic fields generated by the first antenna toward the second antenna and the second antenna choke circuit is configured to limit the propagation of electromagnetic fields generated by the second antenna toward the first antenna.

22. The assembly according to claim 21, wherein the choke conductor electrically connects to the second conductor.

23. The assembly according to claim 21, wherein the length of at least one of the first antenna, the second antenna and the dual-sided choke is related to one-quarter wavelength of one of a first microwave frequency signal and a second microwave frequency signal.

24. The assembly according to claim 21, wherein the first antenna receives a first microwave frequency signal from the proximal portion, the second antenna receives a second microwave frequency signal from the proximal portion and the first and second antenna are configured to simultaneously radiate the first and second microwave frequency signals, respectively.

25. The assembly according to claim 21, further including a dielectric coating disposed at least partially over at least one of the first antenna, the second antenna and the dual-sided choke.

26. The assembly according to claim 21, wherein the first antenna and the second antenna are configured to radiate microwave energy between the distal end of the first antenna and the proximal end of the second antenna.

27. The assembly according to claim 26, wherein the first antenna and the second antenna have a length proportional to the effective wavelength of one of the first microwave frequency signal and the second microwave frequency signal.

28. The assembly according to claim 21, wherein the inner conductor, the outer conductor and the triaxial conductor of the proximal portion are disposed in a triaxial orientation.

29. The assembly according to claim 21, wherein the first antenna includes a first feedpoint and the second antenna includes a second feedpoint, wherein the distance between the midpoint of the first feedpoint and the midpoint of the second feedpoint is related to a quarter wavelength of at least one of the first and second microwave frequency signals.

30. The assembly according to claim 21, wherein at least one of the length of the first antenna choke circuit and the length of the second antenna choke circuit is related to a quarter wavelength of at least one of the first microwave frequency signal and the second microwave frequency signal.

* * * * *